(12) United States Patent
Kobayashi et al.

(10) Patent No.: US 12,083,254 B2
(45) Date of Patent: Sep. 10, 2024

(54) SHIELDING STRUCTURE

(71) Applicant: JGC JAPAN CORPORATION, Kanagawa (JP)

(72) Inventors: Takeshi Kobayashi, Kanagawa (JP); Takeshi Kojima, Kanagawa (JP)

(73) Assignee: JGC JAPAN CORPORATION, Kanagawa (JP)

( * ) Notice: Subject to any disclaimer, the term of this patent is extended or adjusted under 35 U.S.C. 154(b) by 256 days.

(21) Appl. No.: 17/483,816

(22) Filed: Sep. 24, 2021

(65) Prior Publication Data
US 2022/0008600 A1 Jan. 13, 2022

Related U.S. Application Data

(63) Continuation of application No. 16/975,707, filed as application No. PCT/JP2019/018690 on May 10, 2019, now Pat. No. 11,918,712.

(30) Foreign Application Priority Data

Jun. 20, 2018 (JP) ................................. 2018-116967

(51) Int. Cl.
| | | |
|---|---|---|
| *A61L 2/26* | (2006.01) | |
| *A61L 2/08* | (2006.01) | |
| *A61L 9/14* | (2006.01) | |
| *B01D 53/86* | (2006.01) | |
| *B01D 53/88* | (2006.01) | |

(52) U.S. Cl.
CPC ................. *A61L 9/14* (2013.01); *A61L 2/082* (2013.01); *A61L 2/087* (2013.01); *A61L 2/26* (2013.01); *B01D 53/8675* (2013.01); *B01D 53/885* (2013.01); *A61L 2202/11* (2013.01); *A61L 2202/122* (2013.01); *A61L 2202/13* (2013.01);
(Continued)

(58) Field of Classification Search
CPC ............. A61L 2/08; A61L 2/082; A61L 2/087
See application file for complete search history.

(56) References Cited

U.S. PATENT DOCUMENTS 10,920,183 B2 * 2/2021 Zheng .................... C12M 23/10

FOREIGN PATENT DOCUMENTS

| CN | 101417719 | 4/2009 |
|---|---|---|
| CN | 101612522 | 12/2009 |

(Continued)

OTHER PUBLICATIONS

"Lead Sheets." Images Scientific Instruments, www.imagesco.com/geiger/containers.html. Accessed via Wayback Machine, web.archive.org/web/20081223105609/https://www.imagesco.com/geiger/containers.html. Accessed on Aug. 1, 2023. (Year: 2008).*

(Continued)

*Primary Examiner* — Timothy C Cleveland
(74) *Attorney, Agent, or Firm* — JCIPRNET

(57) ABSTRACT

A shielding structure of an object sterilized by radiation. The object is a housing that accommodates an accommodated object therein and is formed of a shielding material that shields the radiation and secondary radiation that has a higher transparency than the radiation and is secondarily generated by the radiation, an exterior of the housing is sterilized by the radiation, and the radiation and the secondary radiation do not penetrate through the accommodated object.

5 Claims, 2 Drawing Sheets

(52) U.S. Cl.
CPC ..... *A61L 2202/23* (2013.01); *B01D 2257/106* (2013.01)

(56) References Cited

FOREIGN PATENT DOCUMENTS

| | | | |
|---|---|---|---|
| CN | 101720233 | 6/2010 | |
| CN | 105039932 | 11/2015 | |
| CN | 107614021 | 1/2018 | |
| CN | 213311939 | 6/2021 | |
| EP | 2578239 | 4/2013 | |
| JP | 2015039684 | 3/2015 | |
| WO | WO-2008057734 A2 * | 5/2008 | ............. A61B 17/00 |
| WO | 2016190088 | 12/2016 | |

OTHER PUBLICATIONS

"Office Action of China Counterpart Application" with English translation thereof, issued on May 16, 2022, p. 1-p. 21.
"Office Action of China Counterpart Application" with English translation thereof, issued on Sep. 14, 2022, p. 1- p. 12.
"Office Action of China Counterpart Application" with English translation thereof, issued on Oct. 10, 2022, p. 1-p. 17.

* cited by examiner

SHIELDING STRUCTURE

CROSS REFERENCE TO RELATED APPLICATIONS

This application is a Continuation of U.S. patent application Ser. No. 16/975,707, filed on Aug. 25, 2020, which claims priority under 35 U.S.C § 119(a) to Patent Application No. 2018-116967, filed in Japan on Jun. 20, 2018, all of which are hereby expressly incorporated by reference into the present application.

TECHNICAL FIELD

The present invention relates to a shielding structure of an object in a bacteria treatment mechanism that irradiates an object with radiation to perform bacteria treatment, and a bacteria treatment method using the bacteria treatment mechanism.

BACKGROUND ART

Conventionally, in order to prevent mixture of bacteria or contamination in a sterile control area when bringing articles from a general control area in which a sterile control is not performed to the sterile control area such as a sterile isolator or a clean room, an apparatus for performing exterior sterilization of the articles is known (for example, see Patent Literature 1). In such an apparatus, the articles arranged in an electron beam irradiation area are irradiated with an electron beam from above and below to sterilize the articles.

Here, in the electron beam irradiation area, ozone ($O_3$) is generated by oxygen ($O_2$) in the air being irradiated with the electron beam. Since this ozone is harmful and needs to be removed from the electron beam irradiation area, an air supply duct and an exhaust duct are connected to the electron beam irradiation area to ventilate the electron beam irradiation area.

CITATION LIST

Patent Literature

Patent Literature 1: WO 03/068272 A

SUMMARY OF INVENTION

Technical Problem

By the way, in the above-mentioned apparatus, although the electron beam irradiation area is sterilized, there is a problem in that the inside of the air supply duct or the exhaust duct is out of the electron beam irradiation area, so that bacteria treatment is not performed. In particular, if the bacteria in the air supply duct are not treated, there is a risk that contaminated air is supplied to the electron beam irradiation area, and the sterilized articles arranged in the electron beam irradiation area are re-contaminated.

The present invention provides a shielding structure capable of reliably sterilizing an exterior of an article.

SOLUTION TO PROBLEM

In the shielding structure of an object sterilized by radiation according to the present invention, the object may be a housing that accommodates an accommodated object therein and is formed of a shielding material that shields the radiation and secondary radiation that has a higher transparency than the radiation and is secondarily generated by the radiation, an exterior of the housing may be sterilized by the radiation, and the radiation and the secondary radiation may not penetrate through the accommodated object.

As a result, in a bacteria treatment process, only the exterior of the housing can be sterilized while protecting the accommodated object from the secondary radiation.

In addition, in the shielding structure according to the present invention, a space inside the housing is maintained in a sterile state.

In addition, in the shielding structure according to the present invention, the housing is formed of lead.

In addition, in the shielding structure of an object sterilized by radiation according to the present invention, the object may be configured to wrap an accommodated object covered with a shielding material that shields the radiation and secondary radiation that has a higher transparency than the radiation and is secondarily generated by the radiation, with a sterile maintaining material that maintains the inside in a sterile state, an exterior of the sterile maintaining material may be sterilized by the radiation, and the radiation and the secondary radiation may not penetrate through the accommodated object.

As a result, in the bacteria treatment process, only the exterior of the sterile maintaining material can be sterilized while protecting the accommodated object from the secondary radiation.

In addition, in the shielding structure according to the present invention, the shielding material is a sheet using lead, and the sterile maintaining material is a plastic bag.

In addition, in the shielding structure of an object sterilized by radiation according to the present invention, the object may be a container that accommodates an accommodated object therein and is formed by providing a layer made of a shielding material that shields the radiation and secondary radiation that has a higher transparency than the radiation and is secondarily generated by the radiation inside a structure, an exterior of the container may be sterilized by the radiation, and the radiation and the secondary radiation may not penetrate through the accommodated object.

As a result, in the bacteria treatment process, only the exterior of the container can be sterilized while protecting the accommodated object from the secondary radiation.

In addition, in the shielding structure according to the present invention, the container has a structure in which a side wall of an upper container covers an outside of a side wall of a lower container at a side surface portion of the container, and the side wall of the upper container and the side wall of the lower container are partially overlap.

In addition, in the shielding structure according to the present invention, a space inside the container is maintained in a sterile state.

In addition, in the shielding structure according to the present invention, the container is a petri dish, and a material containing lead is used for the shielding material.

In addition, in the shielding structure of an object sterilized by radiation according to the present invention, the radiation may be an electron beam and the secondary radiation may be an X-ray.

That is, an electron beam is mainly used as the radiation, and when the radiation is irradiated, X-ray having high transparency is secondarily generated.

Advantageous Effects of Invention

According to the present invention, the present invention can provide the shielding structure of an object sterilized by radiation capable of reliably sterilizing the exterior of the article.

Description of Embodiments

Hereinafter, a bacteria treatment mechanism according to an embodiment of the present invention will be described with reference to the drawings. Note that in the present specification, "sterilization" means that the sterility assurance level (SAL) is less than 10-6. In addition, "decontamination" means that the sterility assurance level (SAL) is less than 10-3. In addition, "bacteria treatment" is meant to include the sterilization and the decontamination.

Figure 1:
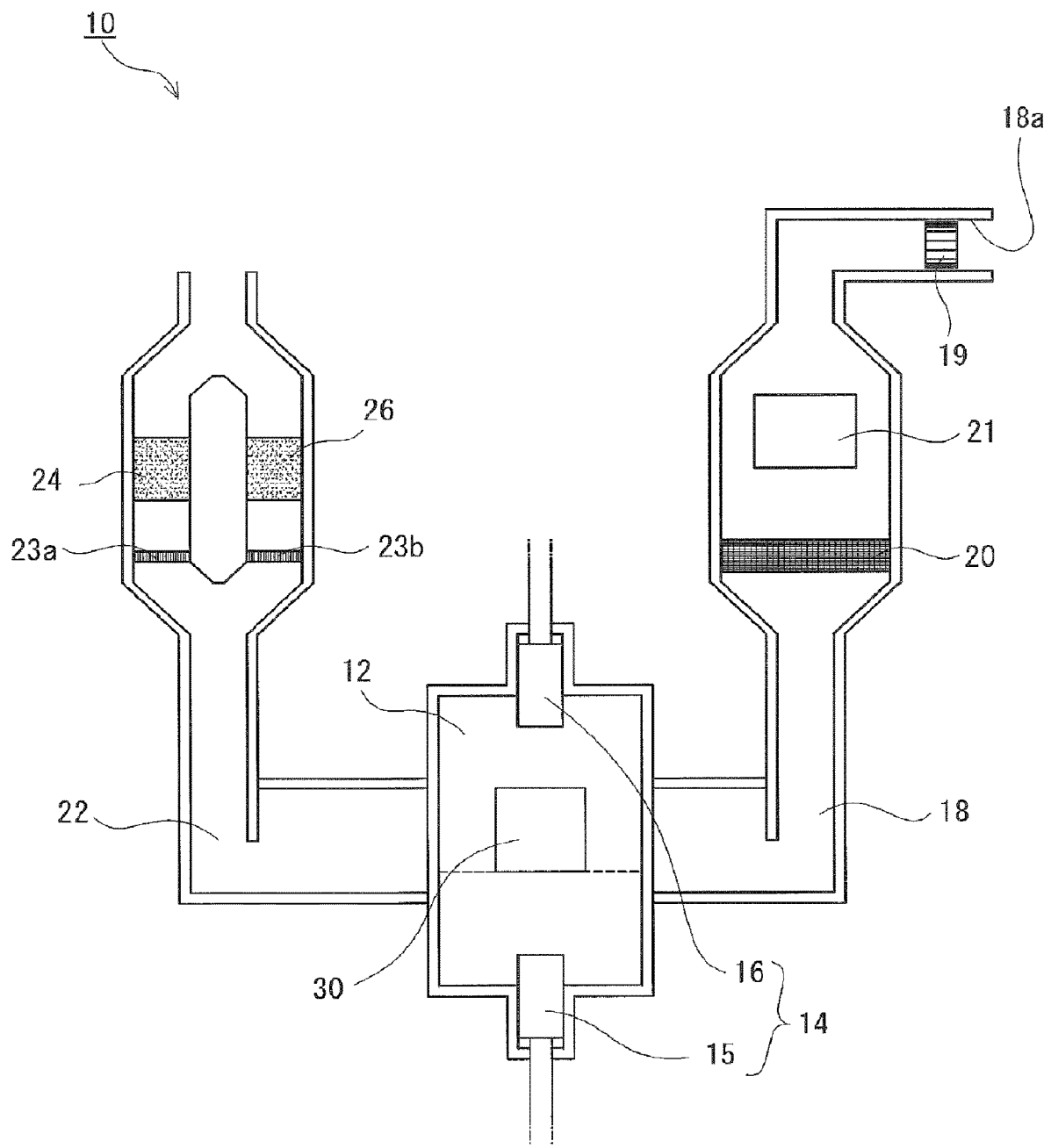
FIG. 1 is a schematic view illustrating a bacteria treatment mechanism according to an embodiment.

FIG. 1 is a schematic view of a bacteria treatment mechanism according to an embodiment. As illustrated in FIG. 1, a bacteria treatment mechanism 10 includes a pass box 12, which is a bacteria treatment unit, an electron beam irradiator 14, which is a radiation irradiation unit, an air supply duct 18, a hydrogen peroxide generator 21, which is a decontamination treatment fluid supply unit, an exhaust duct 22, a first catalyst 24, and a second catalyst 26.

Here, the pass box 12 is a box-shaped apparatus having a space for accommodating an article 30 to be sterilized and having a double door (not illustrated) (a general control area side door and a sterile control area side door) used when the article 30 is taken in and out of a sterile control area. The pass box 12 preferably has a structure in which two doors are not opened at the same time, and has an air lock function for blocking the outside air from the sterile control area.

The electron beam irradiator 14 is an apparatus that irradiates the article 30 with an electron beam for sterilizing the article 30. The electron beam irradiator 14 includes a lower irradiator 15 that irradiates the article 30 with the electron beam from below, and an upper irradiator 16 that irradiates the article 30 with the electron beam from above. In this way, by irradiating the article 30 with the electron beam, an exterior of the article 30 is sterilized in a short time. Note that as the electron beam irradiator 14, only one of the lower irradiator 15 and the upper irradiator 16 may be provided.

Here, in the present embodiment, the electron beam is used as the radiation for performing the bacteria treatment, but the radiation is not limited thereto, and for example, X-rays or gamma rays can be used.

The air supply duct 18 and the exhaust duct 22 are pipes for achieving ventilation in the pass box 12, and are connected to surfaces on which the general control area side door and the sterile control area side door are formed, and left and right surfaces which do not correspond to the surface where the electron beam irradiator 14 is present.

The hydrogen peroxide generator 21 is an apparatus that generates hydrogen peroxide for initial decontamination in the air supply duct 18.

Note that in the present embodiment, for the initial decontamination in the air supply duct 18, the hydrogen peroxide is introduced into the air supply duct 18 as a decontamination treatment fluid, but the decontamination treatment fluid is not limited thereto, and for example, a gas such as an ethylene oxide gas, a formaldehyde gas, nitrogen dioxide, and methanol may be used, and a liquid such as a hydrogen peroxide solution or a peracetic acid solution may be made into a mist and introduced into the air supply duct.

An air supply fan 19 is provided at an air supply port 18a of the air supply duct 18, air is sent from the air supply duct 18 into the pass box 12 by the air supply fan 19, and the pass box 12 is ventilated.

In addition, the air supply duct 18 is preferably provided with an air filter 20 so as to remove dust and dirt contained in the air to be supplied into the pass box 12 and the decontamination treatment fluid. As such an air filter 20, for example, a high efficiency particulate air (HEPA) filter, an ultra low penetration air (ULPA) filter, or the like can be used.

The second catalyst 26 is a catalyst that decomposes ozone generated when oxygen in the air in the pass box 12 is irradiated with the electron beam and converts the ozone into oxygen. The first catalyst 24 is a catalyst that decomposes hydrogen peroxide introduced into the air supply duct 18 into oxygen and water.

The first catalyst 24 in the present embodiment is not particularly limited as long as it is a catalyst capable of detoxifying hydrogen peroxide, for example, "NHO-453" manufactured by JGC Universal Co., Ltd. and the like can be used.

In addition, the second catalyst 26 in the present embodiment is not particularly limited as long as it is a catalyst capable of detoxifying ozone, for example, "NHC-M" and "NHC-R" manufactured by JGC Universal Co., Ltd. can be used.

Note that in the present embodiment, since hydrogen peroxide at the time of initial decontamination and ozone at the time of electron beam irradiation are exhausted, the first catalyst 24 and the second catalyst 26 that decompose hydrogen peroxide and ozone are used, but for example, when an ethylene oxide gas, a formaldehyde gas, or the like is used instead of hydrogen peroxide at the time of initial decontamination, the ethylene oxide gas, the formaldehyde gas, or the like may be used as a detoxifying catalyst.

In addition, in the present embodiment, hydrogen peroxide is treated by the first catalyst 24 and ozone is treated by the second catalyst 26, but for example, like a catalyst described in U.S. Pat. No. 6,180,235, by using a catalyst capable of decomposing both ozone and hydrogen peroxide, it is possible to downside the bacteria treatment mechanism 10 by combining the catalysts into one.

The exhaust duct 22 is provided with dampers 23a and 23b as an exhaust switching mechanism, and the opening and closing of the dampers 23a and 23b can be switched so that during initial decontamination, that is, when hydrogen peroxide (molecules) is exhausted from the pass box 12 to the exhaust duct 22, the damper 23a is opened so that the exhaust gas is guided to the first catalyst 24, and in addition, during sterilization by electron beam irradiation, that is, when ozone (molecules) is exhausted from the pass box 12 to the exhaust duct 22, the damper 23b is opened so that the exhaust gas is guided to the second catalyst 26.

Next, a series of treatments of the bacteria treatment mechanism 10 will be described. First, in an initial state, hydrogen peroxide is generated by the hydrogen peroxide generator 21 and introduced into the air supply duct 18. When the hydrogen peroxide is introduced into the air supply duct 18, the inside of the air supply duct 18 is decontaminated by the hydrogen peroxide (initial decontamination process). In this way, by preliminarily decontaminating the inside of the air supply duct 18 in the initial state, uncontaminated air can be sent into the pass box 12 during ventilation.

Next, the air supply fan 19 supplies air through the air supply duct 18 (initial air supply process). The air and hydrogen peroxide in the air supply duct 18 and the pass box 12 are guided to the catalyst via the exhaust duct 22 (initial decomposition process). Here, the hydrogen peroxide is decomposed by the first catalyst 24 and then released to the outside air.

Once the initial decontamination is complete, the article 30 can be sterilized. When sterilizing the article 30, first, the general control area side door is opened and the article 30 is carried into the pass box 12. Next, when the general control area side door is closed, electron beams are emitted from the upper irradiator 16 and the lower irradiator 15, and the article 30 is irradiated with the electron beams from both upper and lower sides. As a result, the exterior of the article 30 is sterilized (bacteria treatment process). Note that when the article 30 is irradiated with the electron beam, oxygen ($O_2$) in the air existing in an irradiation area in the pass box 12 is irradiated with the electron beam, so that ozone ($O_3$) is generated.

After the sterilization treatment, air is supplied into the pass box 12 via the air supply duct 18 by an air supply unit (not illustrated), and the air in the pass box 12 and ozone are exhausted to the exhaust duct 22 (aeration process). Ozone is decomposed by the second catalyst 26 and then released to the outside air (decomposition process). Thereafter, the sterile control area side door is opened, and the sterilized article 30 is taken out from the pass box 12 (take-out process).

Note that in order to prevent recontamination, it is preferable to sterilize the article 30 after completion of the initial decontamination and continuously supply the air through the air supply duct 18 until the sterilized article 30 is taken out from the pass box 12.

According to the bacteria treatment mechanism 10 of the present embodiment, by preliminarily performing initial decontamination for the inside of the air supply duct 18 with hydrogen peroxide, air contaminated with bacteria is not introduced into the pass box 12, recontamination of the sterilized article 30 can be prevented, and the exterior of the article 30 can be reliably sterilized. In addition, since hydrogen peroxide used in the initial decontamination and ozone generated in the pass box 12 are decomposed by the catalysts and exhausted, it is possible to prevent air in the surrounding environment from being contaminated.

Note that when the article 30 is irradiated with the electron beam, X-rays (secondary radiation) may be secondarily generated. In this case, since a transparency of the X-rays is higher than that of the electron beam, it is necessary to consider the influence of X-rays. Hereinafter, this will be described step by step.

First, when the article 30 is not affected by either the electron beam or X-rays, the exterior of the article 30 is sterilized by the electron beam in the bacteria treatment process by irradiating the article 30 with the electron beam as described above. Here, as the article 30, small jigs such as a spoon may be considered.

In addition, when the article 30 includes contents affected by either the electron beam or the X-rays, various modes are conceivable for the article 30 in the above-described embodiment. For example, as an example of the case where the content of the article 30 is not affected by the X-rays but is affected by the electron beam, the article 30 is assumed to be one in which the content is covered with a resin container or a plastic bag. In this case, the electron beam can be shielded by the resin container or the plastic bag, and the electron beam can be prevented from penetrating the content. Note that in the bacteria treatment process, an exterior of the resin container or the plastic bag is sterilized by the electron beam.

Figure 2:
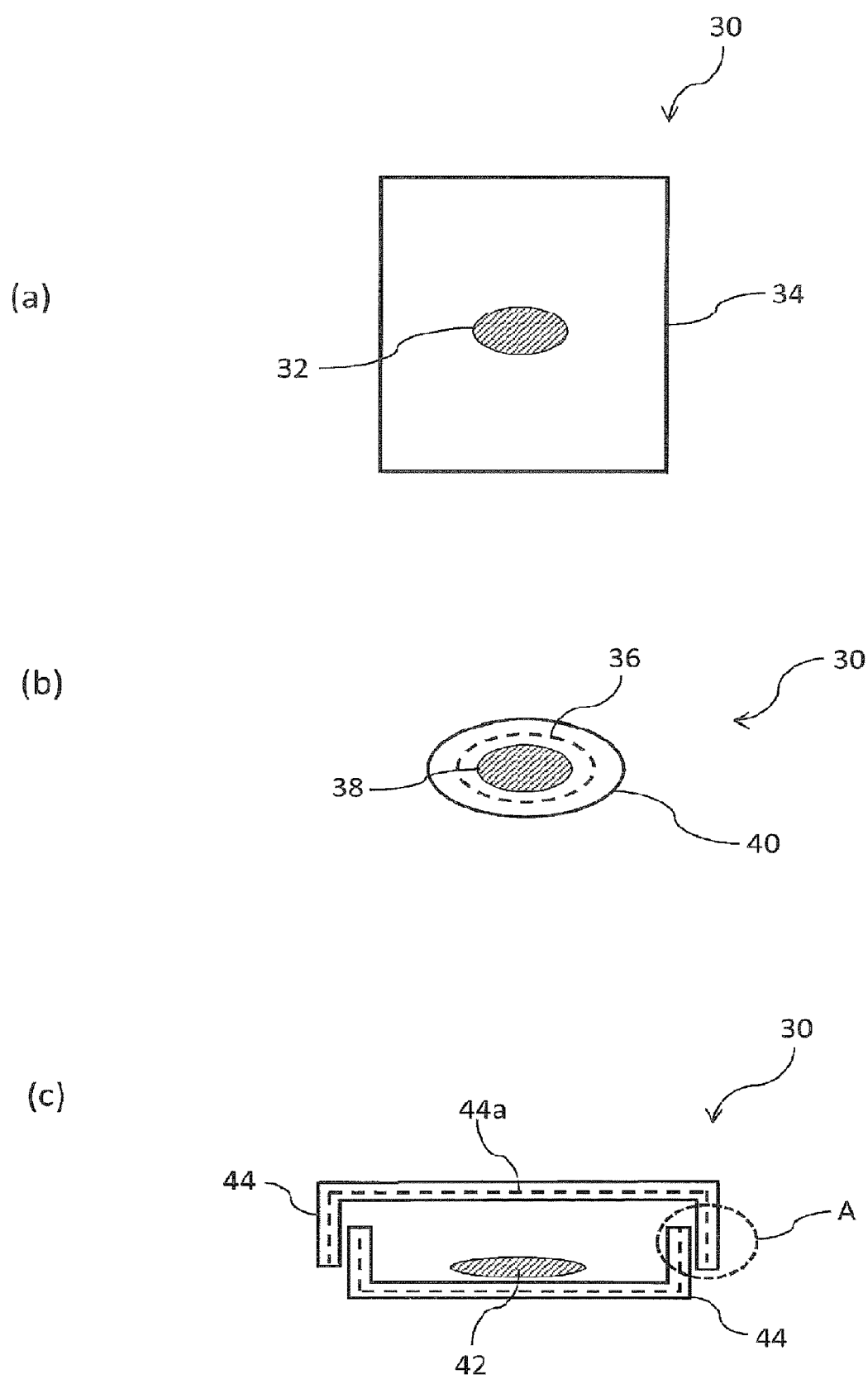
FIG. 2 is a view illustrating a pattern of an article including an accommodated object in the bacteria treatment mechanism according to the embodiment.

In addition, as an example of the case where the content of the article 30 is affected by both the electron beam and the X-rays, the cases illustrated in each of FIG. 2 are assumed as follows. For example, as illustrated in (a) of FIG. 2, the article 30 may be a housing 34 that accommodates an accommodated object 32 therein. Here, the housing 34 has a function of maintaining sterility, and a space inside the housing 34 is maintained in a sterile state. In addition, the housing 34 is formed of a shielding material such as lead that shields the electron beam and the X-rays. Therefore, in the bacteria treatment process, only an exterior of the housing 34 is sterilized, and the penetration of the electron beam and the X-rays into the accommodated object 32 is prevented. Note that as a specific example of the accommodated object 32, for example, a pipetter or the like can be considered.

In addition, as illustrated in (b) of FIG. 2, the article 30 may be one in which an accommodated object 38 covered with a shielding material 36 is wrapped with a sterile maintaining material 40. Note that the inside of the sterile maintaining material 40 is maintained in a sterile state. Here, when the article 30 is irradiated with the electron beam, the electron beam is shielded by the sterile maintaining material 40, but the secondarily generated X-rays penetrate through the sterile maintaining material 40. However, the X-rays that have penetrated through the sterile maintaining material 40 are shielded by the shielding material 36. Therefore, in the bacteria treatment process, only an exterior of the sterile maintaining material 40 is sterilized, and the penetration of the X-rays into the accommodated object 38 is prevented. Note that an electron beam having a high velocity may penetrate through the sterile maintaining material 40, but in this case also, the electron beam is shielded by the shielding material 36. In addition, as the sterile maintaining material 40, for example, a material capable of maintaining the sterile state, such as a plastic bag or a Tyvek® sheet (flashspun high-density polyethylene fibers) is considered, and as the shielding material 36, a sheet using lead is considered.

In addition, as illustrated in (c) of FIG. 2, the article 30 may be a container 44 that accommodates an accommodated object 42 therein. Here, the container 44 is made of a composite material in which a layer made of a shielding material 44a is provided in a structure, and has a function of shielding the electron beam and the X-rays. Therefore, in the bacteria treatment process, only an exterior of the container 44 is sterilized, and the penetration of the electron beam and the X-rays into the accommodated object 42 is prevented. Further, the container 44 also has a function of maintaining sterility inside. Therefore, a space inside the container 44 is maintained in the sterile state. Note that as the container 44, for example, a petri dish is assumed, and a material containing lead or the like is used for a shielding material 44*a*. In addition, as the accommodated object 42, for example, a cell is considered.

Note that the container 44 illustrated in (c) of FIG. 2 has a shape in which a side wall of the upper container 44 covers the outside of a side wall of the lower container 44 at a side surface portion A thereof. In this way, when the upper and lower side walls partially overlap, since the X-rays are reflected and attenuated in gaps between the side walls, it is possible to accurately shield the X-rays even if there are gaps in the side walls. When more attenuation is required, the X-rays can be accurately shielded by adding a structure that partially bends a path of the gap.

Although the preferred embodiment of the present invention has been described above, the present invention is not limited thereto, and various modifications can be made without departing from the object of the present invention, such as, for example, in the above-described embodiment, the description was given as an example applied to the pass box, but it can also be applied to a glove box or an isolator, or a continuous sterilization system as disclosed in Patent Literature 1, and the like.

The invention claimed is:

1. An article sterilized by radiation, the article comprising a shielding structure, wherein the shielding structure comprising:
    a container that accommodates an accommodated object therein, and
    a shielding material layer that shields the radiation and secondary radiation that has a higher transparency than the radiation and is secondarily generated by the radiation,
    wherein the container is a petri dish,
    the container has an upper portion and a lower portion, and the shielding material layer is interposed between an inner surface of the upper portion of the container and an outer surface of the upper portion of the container, and between an inner surface of the lower portion of the container and an outer surface of the lower portion of the container,
    an exterior of the container is sterilized by the radiation, and
    the radiation and the secondary radiation do not penetrate through the accommodated object.

2. The shielding structure according to claim 1, wherein the container has a structure in which a side wall of the upper portion of the container covers an outside of a side wall of the lower portion of the container at a side surface portion of the container, and the side wall of the upper portion of the container and the side wall of the lower portion of the container are partially overlap.

3. The shielding structure according to claim 1, wherein a space inside the container is maintained in a sterile state.

4. The shielding structure according to claim 1, wherein a material containing lead is used for the shielding material layer.

5. The shielding structure according to claim 1, wherein the radiation is an electron beam and the secondary radiation is an X-ray.

* * * * *